United States Patent [19]

Kristinsson

[11] 4,448,968
[45] May 15, 1984

[54] PROCESS FOR THE PREPARATION OF 1,3,4-THIADIAZOLONE DERIVATIVES

[75] Inventor: Haukur Kristinsson, Bottmingen, Switzerland

[73] Assignee: Ciba-Geigy Corporation, Ardsley, N.Y.

[21] Appl. No.: 351,095

[22] Filed: Feb. 23, 1982

[30] Foreign Application Priority Data

Feb. 27, 1981 [CH] Switzerland ............ 1336/81

[51] Int. Cl.³ .............................. C07D 285/12
[52] U.S. Cl. ................... 548/136; 544/333; 546/144; 546/167; 546/277; 548/141
[58] Field of Search ......... 548/136, 141; 546/277, 546/167, 144; 544/333

[56] References Cited

FOREIGN PATENT DOCUMENTS 1415605 9/1965 France .
394696 12/1965 Switzerland .

OTHER PUBLICATIONS

Tomita et al., "Synthesis of acid hydrazide derivatives containing . . . ", Abstract *CA49*:11591a (1955).
Lawson et al., "Cyclisation of some thiobenzamido-compounds", *J. Chem. Soc.* [1957], 1556–1561.
Weidinger, "Synthesen mit Imidsäureestern, II, Syntheses von 1,3,4-Thiodiazulen", *Chem. Ber.* 96, 1059–1063 (1963).
Akerblom et al., "Synthesis of 2-alkoxy-1,3,4-thiadiazoles", *Acta. Chem. Scan.* 18, 174–184 (1964).
Japan-Patent Appl. No. 29676/64—Abstract *C.A.* 66, 85794x (1967).
Clarkson et al., "2-Alkoxy-5-amino- and —5-arenesulphonamido-1,3,4-thiadiazoles . . . ", *J. Chem. Soc.* [1967], 2700–2704.
Rüfenacht, "Zur Chemie von GS 13005, einem neuen insektiziden Phosphorsäureester", *Helv. Chim. Acta* 51, 518–526 (1968).
Rüfenacht, "Arbeiten über Phosphorsäure-und Thiophosphorsäureester mit . . . ", *Helv. Chim. Acta.* 55, 1979–1986 (1972).

*Primary Examiner*—Mary C. Lee
*Attorney, Agent, or Firm*—Frederick H. Rabin; Bruce M. Collins

[57] ABSTRACT

A process for preparing 1,3,4-thiadiazolone compounds of the formula

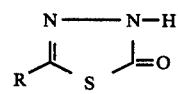

comprising reacting a 2-alkoxy-1,3,4-thiadiazole of the formula

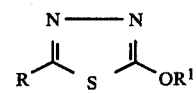

with hydrogen chloride in non-aqueous organic solvent under non-aqueous conditions at a temperature of from 0° to 100° C.

3 Claims, No Drawings

PROCESS FOR THE PREPARATION OF 1,3,4-THIADIAZOLONE DERIVATIVES

The present invention relates to a novel process for the preparation of 1,3,4-thiadiazol-2(3H)-one derivatives of the formula I

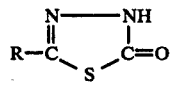
(I)

in which R is hydrogen, alkyl having 1 to 12 carbon atoms, alkenyl having 2 to 8 carbon atoms, cycloalkyl having 3 to 8 carbon atoms, halogenoalkyl having 1 to 8 carbon atoms and 1 to 4 halogen atoms, halogenoalkenyl having 2 to 8 carbon atoms and 1 to 4 halogen atoms, cyanoalkyl having 1 to 6 carbon atoms in the alkyl moiety, amino, alkylamino having 1 to 6 carbon atoms, dialkylamino having a total of 2 to 8 carbon atoms in the alkyl moieties, alkoxyalkyl having a total of 2 to 8 carbon atoms, alkoxycarbonyl having 1 to 6 carbon atoms in the alkyl moiety, alkylthioalkyl having a total of 2 to 8 carbon atoms, alkylsulfinylalkyl having a total of 2 to 8 carbon atoms, alkylsulfonylalkyl having a total of 2 to 8 carbon atoms, alkylaminoalkyl having a total of 2 to 12 carbon atoms and 1 to 3 amino groups, alkylaminocarbonyl having 1 to 6 carbon atoms in the alkyl moiety, dialkylaminocarbonyl having 2 to 12 carbon atoms in the alkyl moieties, it being possible for the two alkyl groups, together with the adjacent nitrogen atom, to form a ring which has 5 to 6 ring atoms and which can contain a second hetero-atom (oxygen or nitrogen atom), or is phenylaminoalkyl which has 1 to 6 carbon atoms in the alkyl moiety and has a phenyl moiety which is unsubstituted, or monosubstituted or disubstituted by halogen, alkyl having 1 to 4 carbon atoms, trifluoromethyl, alkoxy having 1 to 4 carbon atoms, alkylthio having 1 to 4 carbon atoms, phenyl, phenoxy, cyano or nitro, or is unsubstituted phenyl or phenyl which is monosubstituted or disubstituted by halogen, alkyl having 1 to 4 carbon atoms, trifluoromethyl, alkoxy having 1 to 4 carbon atoms, alkylthio having 1 to 4 carbon atoms, phenyl, phenoxy, cyano or nitro, or is phenylalkyl which has 1 to 6 carbon atoms in the alkyl moiety and has a phenyl moiety which is unsubstituted, or monosubstituted or disubstituted by halogen, alkyl having 1 to 4 carbon atoms, trifluoromethyl, alkoxy having 1 to 4 carbon atoms, alkylthio having 1 to 4 carbon atoms, phenyl, phenoxy, cyano or nitro, or is phenoxyalkyl which has 1 to 4 carbon atoms in the alkyl moiety and has a phenyl moiety which is unsubstituted, or monosubstituted or disubstituted by halogen, alkyl having 1 to 4 carbon atoms, trifluoromethyl, alkoxy having 1 to 4 carbon atoms, alkylthio having 1 to 4 carbon atoms, phenyl, phenoxy, cyano or nitro, or is phenalkenyl which has 2 to 4 carbon atoms in the alkenyl moiety and has a phenyl moiety which is unsubstituted, or monosubstituted or disubstituted by halogen, alkyl having 1 to 4 carbon atoms, trifluoromethyl, alkoxy having 1 to 4 carbon atoms, alkylthio having 1 to 4 carbon atoms, phenyl, phenoxy, cyano or nitro, or is alkoxycarbonylalkyl having a total of 3 to 9 carbon atoms in the alkyl moieties or a hetero-aromatic ring having 5 or 6 ring atoms, 1 to 3 of which are hetero-atoms.

The novel process is preferably used for the preparation of compounds of the formula Ia

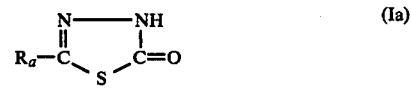
(Ia)

in which $R_a$ is hydrogen, alkyl having 1 to 6 carbon atoms, alkenyl having 2 to 3 carbon atoms, cycloalkyl having 3 to 6 carbon atoms, halogenoalkyl having 1 to 4 carbon atoms and 1 to 3 halogen atoms, halogenoalkenyl having 2 to 3 carbon atoms and 1 or 2 halogen atoms, cyanoalkyl having 1 to 2 carbon atoms in the alkyl moiety, amino, alkylamino having 1 to 3 carbon atoms, dialkylamino having a total of 2 to 4 carbon atoms in the alkyl moieties, alkoxyalkyl having a total of 2 or 3 carbon atoms, alkoxycarbonyl having 1 to 3 carbon atoms in the alkyl moiety, alkylthioalkyl having a total of 2 or 3 carbon atoms, alkylsulfinylalkyl having a total of 2 or 3 carbon atoms, alkylsulfonylalkyl having a total of 2 or 3 carbon atoms, alkylaminoalkyl having a total of 2 to 6 carbon atoms and 1 or 2 amino groups, alkylaminocarbonyl having 1 to 3 carbon atoms in the alkyl moiety, dialkylaminocarbonyl having 2 to 6 carbon atoms in the alkyl moieties, it being possible for the two alkyl groups, together with the adjacent nitrogen atom, to form a ring which has 5 to 6 ring atoms and can contain a second hetero-atom (oxygen or nitrogen atom), or is phenylaminoalkyl which has 1 to 3 carbon atoms in the alkyl moiety and has a phenyl moiety which is unsubstituted, or monosubstituted or disubstituted by halogen, alkyl having 1 to 4 carbon atoms, trifluoromethyl, alkoxy having 1 to 4 carbon atoms, alkylthio having 1 to 4 carbon atoms, phenyl, phenoxy, cyano or nitro, or is unsubstituted phenyl or phenyl which is monosubstituted or disubstituted by halogen, alkyl having 1 to 4 carbon atoms, trifluoromethyl, alkoxy having 1 to 4 carbon atoms, alkylthio having 1 to 4 carbon atoms, phenyl, phenoxy, cyano or nitro, or is phenylalkyl which has 1 or 2 carbon atoms in the alkyl moiety and has a phenyl moiety which is unsubstituted, or monosubstituted or disubstituted by halogen, alkyl having 1 to 4 carbon atoms, trifluoromethyl, alkoxy having 1 to 4 carbon atoms, alkylthio having 1 to 4 carbon atoms, phenyl, phenoxy, cyano or nitro, or is phenoxyalkyl which has 1 or 2 carbon atoms in the alkyl moiety and has a phenyl moiety which is unsubstituted, or monosubstituted or disubstituted by halogen, alkyl having 1 to 4 carbon atoms, trifluoromethyl, alkoxy having 1 to 4 carbon atoms, alkylthio having 1 to 4 carbon atoms, phenyl, phenoxy, cyano or nitro, or is phenalkenyl which has 2 to 4 carbon atoms in the alkenyl moiety and has a phenyl moiety which is unsubstituted, or monosubstituted or disubstituted by halogen, alkyl having 1 to 4 carbon atoms, trifluoromethyl, alkoxy having 1 to 4 carbon atoms, alkylthio having 1 to 4 carbon atoms, phenyl, phenoxy, cyano or nitro, or is alkoxycarbonylalkyl having a total of 3 to 6 carbon atoms in the alkyl moieties or a hetero-aromatic ring having 5 or 6 ring atoms, 1 to 3 of which are hetero-atoms.

Furthermore, the novel process is very particularly suitable for the preparation of compounds of the formula Ib

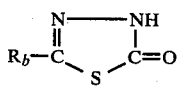

in which $R_b$ is hydrogen, alkyl having 1 to 6 carbon atoms, cycloalkyl having 3 to 6 carbon atoms, halogenoalkyl having 1 to 4 carbon atoms and 1 to 3 halogen atoms, cyanoalkyl having 1 or 2 carbon atoms in the alkyl moiety, amino, alkylamino having 1 to 3 carbon atoms, dialkylamino having 2 to 4 carbon atoms in the alkyl moieties, alkoxyalkyl having a total of 2 to 3 carbon atoms, alkoxycarbonyl having 1 to 3 carbon atoms in the alkyl moiety, alkylthioalkyl having a total of 2 to 3 carbon atoms, alkylaminoalkyl having a total of 2 to 6 carbon atoms and 1 amino group, phenylaminoalkyl which has 1 to 3 carbon atoms in the alkyl moiety and has a phenyl moiety which is unsubstituted, or monosubstituted or disubstituted by halogen, alkyl having 1 to 4 carbon atoms, trifluoromethyl, alkoxy having 1 to 4 carbon atoms, alkylthio having 1 to 4 carbon atoms, phenyl, phenoxy, cyano or nitro, or is unsubstituted phenyl or phenyl which is monosubstituted or disubstituted by halogen, alkyl having 1 to 4 carbon atoms, trifluoromethyl, alkoxy having 1 to 4 carbon atoms, alkylthio having 1 to 4 carbon atoms, phenyl, phenoxy, cyano or nitro, or is benzyl having a phenyl moiety which is unsubstituted, or monosubstituted or disubstituted by halogen, alkyl having 1 to 4 carbon atoms, trifluoromethyl, alkoxy having 1 to 4 carbon atoms, alkylthio having 1 to 4 carbon atoms, phenyl, phenoxy, cyano or nitro, or is phenoxymethylene having a phenyl moiety which is unsubstituted, or monosubstituted or disubstituted by halogen, alkyl having 1 to 4 carbon atoms, trifluoromethyl, alkoxy having 1 to 4 carbon atoms, alkylthio having 1 to 4 carbon atoms, phenyl, phenoxy, cyano or nitro, or is phenalkenyl which has 2 carbon atoms in the alkenyl moiety and has a phenyl moiety which is unsubstituted, or monosubstituted or disubstituted by halogen, alkyl having 1 to 4 carbon atoms, trifluoromethyl, alkoxy having 1 to 4 carbon atoms, alkylthio having 1 to 4 carbon atoms, phenyl, phenoxy, cyano or nitro, or is alkoxycarbonylalkyl having a total of 3 to 6 carbon atoms in the alkyl moieties or a hetero-aromatic ring having 5 or 6 ring atoms, one of which is a hetero-atom.

The halogen in the definition of R can be fluorine, chlorine, bromine or iodine, and fluorine and chlorine are regarded as preferred.

The hetero-atoms of the hetero-aromatic ring R are oxygen, nitrogen or sulfur atoms. Hetero-aromatic rings are understood to be rings having 5 or 6 ring atoms, 1 or 2 of which are hetero-atoms, for example furan, thiophene, pyrrole, isoxazole, oxazole, thiazole, isothiazole, pyridine or pyrimidine and also benzo-fused heteroaromatics, such as benzofuran, benzothiophene, indole, quinoline or isoquinoline.

The 1,3,4-thiadiazol-2(3H)-one derivatives of the formula I represent valuable intermediates, since they can be used for the preparation of pesticides, such as insecticides, acaricides and fungicides, and also of pharmaceuticals. The accessibility of these classes of active ingredients is substantially improved by the process according to the invention.

1,3,4-Thiadiazol-2(3H)-ones of the formula I can, for example, be used for the preparation of analogues of the insecticidal and acaricidal commercial product supracid (ultracid) (Helv. Chim. Acta 51 (1968) 518–526; Swiss Patent Specification No. 394,696), by converting compounds of the formula I with formaldehyde into the hydroxymethyl derivatives and then reacting the latter with dithiophosphates.

A number of fungicidal 3-trichloromethylmercapto-1,3,4-thiadiazol-2(3H)-one derivatives can also be prepared by the action of trichloromethylmercapto chloride on the corresponding compounds of the formula I (U.S. Pat. No. 3,202,673).

Moreover, insecticidally active N-substituted 3-carbamoyl-1,3,4-thiadiazol-2(3H)-one derivatives can be prepared by reacting the corresponding compounds of the formula I with N-substituted carbamoyl chlorides in the presence of tertiary bases (French Patent Specification No. 1,415,605).

Furthermore, 1,3,4-thiadiazol-2(3H)-one derivatives having effective pharmacological properties against tuberculosis are accessible via compounds of the formula I (c.f. Japanese Patent Application No. 29,676/64.

Hitherto, compounds of the formula I have been prepared by cyclising N-carbamoylthiohydrazides by means of heating, in the presence or absence of additives, such as concentrated hydrochloric acid or polyphosphoric acid (J. Chem. Soc. 1957, 1556–61). A process is also known in which thiocarbazic acid derivatives can be reacted with phosgene, with cyclisation to give compounds of the formula I (Helv. 51 (1968), 518–526). The utility of the above processes in practice is reduced especially by the fact that, in particular, these processes enable only a very restricted number of derivatives of the formula I to be prepared, because the thiohydrazide compounds required as starting material for the processes are not at all readily accessible.

According to a further known process, compounds of the formula I can be obtained by heating 2-methylsulfonyl-1,3,4-thiadiazole derivatives in the presence of dilute sodium hydroxide solution (Chem. Abstr. 49 (1955), 11952). This process has the disadvantage that it comprises several process steps, including the oxidation of a methylthio substituent to a methylsulfonyl substituent on the 1,3,4-thiadiazole ring and thus requires considerable expense. Moreover, these reactions are carried out in an aqueous medium and, in view of the sensitivity of the hetero-ring to hydrolysis, this represents an additional disadvantage.

Using another known process, the 5-amino derivative of the formula I can be prepared by heating 2-ethoxy-5-amino-1,3,4-thiadiazole in 2 N hydrochloric acid for 4 hours under reflux (Acta Chem. Scand. 18 (1964), 177–183). This known process gives the abovementioned compound in a yield of about 50%. If the reaction time is prolonged substantially beyond 4 hours, however, this process does not give the desired result, but thiosemicarbazide is obtained as the final product, the hetero-ring being split open and $CO_2$ being liberated.

The process, according to the invention, for the preparation of the compounds of the formula I, by means of which the disadvantages of the known processes for the preparation of compounds of the formula I can be overcome in an advantageous manner, is carried out by allowing compounds of the formula II

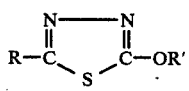
(II)

in which R is as defined under the formula I and R' is alkyl having 1 to 4 carbon atoms, to react in organic solvents at 0° to 100° C. in the presence of hydrogen chloride. The compounds of the formula I are thus formed, in addition to the alkyl chlorides R'Cl.

Temperatures of 20° to 60° C. are to be regarded as the preferred reaction temperatures for the process according to the invention.

Examples of organic solvents suitable for carrying out the process according to the invention are ethers, such as diethyl ether or dioxane, chlorinated hydrocarbons, such as chloroform or methylene chloride, or alcohols, such as methanol, ethanol or isopropanol.

The process according to the invention is distinguished especially by its simplicity in practice and the high yields obtained. Compared with the known processes, it represents important improvements and advantages, since almost quantitative conversion of the reactants takes place even at a reaction time of a few hours and under very mild conditions. Generally, yields of more than 95%, relative to the starting material, are obtained. A particular feature of the process according to the invention is that the novel process is carried out with exclusion of water, and this is a great advantage in view of the sensitivity of the 1,3,4-thiadiazole derivatives to hydrolysis. The instability of these compounds in the presence of water not only concerns the 1,3,4-thiadiazole ring generally, but it can also be reinforced by some of the radicals defined as constituents, and this means that the preparation of compounds of the formula I by the hitherto known processes is made particularly difficult or even prevented. These difficulties are avoided by the process according to the invention.

The starting compounds of the formula II can be prepared by known processes, by reacting O-methyl thiocarbazates with carboxylic acid derivatives, such as imino-esters or ortho-esters (c.f. Chem. Ber. 96 (1963) 1059), or first reacting them with an acid chloride and then treating the resulting acyl derivative of O-methyl thiocarbazate with concentrated sulfuric acid (c.f. Helv. chim. acta 55 (1972) 1979–86). The 2-methoxy-5-aminothiazole compound of the formula II can be prepared from O-methyl thiocarbazate and cyanogen chloride (c.f. J. Chem. Soc. 2700, 1967).

The process according to the invention is explained in more detail by reference to the examples which follow and which include the preparation of the starting compounds.

EXAMPLE 1

(a) Preparation of 2-methoxy-1,3,4-thiadiazole 21.2 g (0.2 mol) of O-methyl thiocarbazate and 24.1 g (0.22 mol) of ethyl formimidate are boiled under reflux for 12 hours in 150 ml of dioxan. After cooling, the reaction mixture is filtered, evaporated and distilled in a high vacuum.

This gives 21 g of 2-methoxy-1,3,4-thiadiazole as a colourless oil. Boiling point: 48° C./0.27 mbar.

The same product is obtained in a similar yield by boiling 21.2 g (0.2 mol) of O-methyl thiocarbazate with 29.6 g (0.2 mol) of triethyl ortho-formate under reflux for 4 hours in 100 ml of dioxan.

(b) Preparation of 1,3,4-thiadiazol-2(3H)-one 26 g (0.2 mol) of 2-methoxy-1,3,4-thiadiazole are introduced into a solution of 10 g of hydrogen chloride in 200 ml of diethyl ether. After boiling for one hour under reflux, the mixture is evaporated and the resulting solid mass is slurried with a little cold chloroform and filtered off. This gives 20 g of 1,3,4-thiadiazol-2(3H)-one. Melting point: 98° C.; yield: 98% of theory.

EXAMPLE 2

(a) Preparation of 2-methoxy-5-phenoxymethyl-1,3,4-thiadiazole 21.2 g (0.2 mol) of O-methyl thiocarbazate and 47 g (0.22 mol) of ethyl phenoxyacetimidate are heated for 12 hours under reflux in 150 ml of dioxan.

After cooling and filtering off, the mixture is evaporated and the resulting oil is taken up in ether. The ether solution is washed with water, then dried and evaporated. The resulting oil solidifies on standing.

This gives 44 g of 2-methoxy-5-phenoxymethyl-1,3,4-thiadiazole as a crude product.

(b) Preparation of 5-phenoxymethyl-1,3,4-thiadiazol-2(3H)-one 44 g of crude 2-methoxy-5-phenoxymethyl-1,3,4-thiadiazole are added in portions to a solution of 15 g of hydrogen chloride in 200 ml of dioxane. After boiling for one hour under reflux, the mixture is evaporated and the resulting mass is recrystallised from a little methanol. This gives 30 g of 5-phenoxymethyl-1,3,4-thiadiazol-2(3H)-one as colourless crystals.

Melting point: 104°–105° C.; yield: 91% of theory.

EXAMPLE 3

(a) Preparation of 2-methoxy-5-trifluoroacetyl-1,3,4-thiadiazole 20.2 g (0.1 mol) of O-methyl 1-trilfuoroacetylthiocarbazate (sic) are introduced into 100 ml of concentrated sulfuric acid, while cooling with ice water. After stirring for 1 hour, the mixture is poured onto ice, and the oil which has separated out is taken up with ether. The ether solution is dried and evaporated, and the resulting oil is distilled in vacuo. This gives 16 g of 2-methoxy-5-trifluoromethyl-1,3,4-thiadiazole as a colourless oil.

Boiling point: 55° C./18.7 mbar.

(b) Preparation of 5-trifluoromethyl-1,3,4-thiadiazol-2(3H)-one 18.4 g (0.1 mol) of 2-methoxy-5-trifluoromethyl-1,3,4-thiadiazole are introduced into a solution of 10 g of hydrogen chloride in 100 ml of dioxane. The reaction mixture is left to stand for a few hours and then completely evaporated, and the resulting solid product is recrystallised from hexane or distilled.

This gives 15 g of 5-trifluoromethyl-1,3,4-thiadiazol-2(3H)-one. Melting point: 54°–55° C.; boiling point: 55° C./18.7 mbar; yield: 88% of theory.

EXAMPLE 4

Preparation of 5-amino-1,3,4-thiadiazol-2(3H)-one 26.2 g of 2-amino-5-methoxy-1,3,4-thiadiazole, prepared from O-methyl thiocarbazate and cyanogen chloride (J. Chem. Soc. (C) 2700, 1967), are introduced into a solution of 20 g of hydrogen chloride in 200 ml of dioxane, and the mixture is heated for several hours at 50°-60° C.

After evaporation, the resulting solid mass is slurried with ether and filtered off.

The product can be recrystallised from water.

This gives 18 g of 5-amino-1,3,4-thiadiazol-2(3H)-one.

Melting point: 172° C. (literature Acta Chem. Scand. 18 (1964) 174: 170°-174° C.). Yield: 77% of theory.

The following compounds were prepared analogously to the examples illustrated above:

TABLE 1

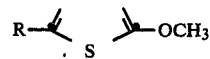

| No. | R | Physical Data |
|---|---|---|
| 1 | methyl | melting point 95° C. |
| 2 | H | melting point 98° C. |
| 3 | isopropyl | oil |
| 4 | n-butyl | oil |
| 5 | tert.-butyl | oil |
| 6 | vinyl | melting point 40° C. |
| 7 | chloromethyl | melting point 87° C. |
| 8 | trichloromethyl | melting point 130° C. |
| 9 | 1-chloroethyl | oil |
| 10 | 2-chloroethyl | oil |
| 11 | trifluoromethyl | boiling point: 55°/18.7 mbar |
| 12 | cyanomethyl | melting point 65° C. |
| 13 | methoxymethyl | melting point 47° C. |
| 14 | 2-methoxyethyl | oil |
| 15 | ethoxycarbonylmethyl | melting point 79° C. |
| 16 | amino | melting point 172° C. |
| 17 | phenoxymethyl | melting point 104°-106° C. |
| 18 | 4-chlorophenoxymethyl | melting point 149°-151° C. |
| 19 | 2,3-dimethylphenoxymethyl | melting point 163°-165° C. |
| 20 | 3,5-dichlorophenoxymethyl | melting point 114°-116° C. |
| 21 | 2-methyl-4-chlorophenoxymethyl | melting point 176°-178° C. |
| 22 | 2,6-dimethylphenoxymethyl | |
| 23 | 4-tert.-butylphenoxymethyl | melting point 139° C. |
| 24 | benzyl | melting point 95° C. |
| 25 | 4-chlorobenzyl | melting point 110° C. |
| 26 | 3,4-dichlorobenzyl | melting point 108° C. |
| 27 | 2,4-dichlorobenzyl | melting point 123° C. |
| 28 | 3-trifluoromethylbenzyl | melting point 76° C. |
| 29 | 3,4-dichloro-α-ethyl-benzyl | oil |
| 30 | styryl | melting point 170°-171° C. |
| 31 | 2-(fur-2-yl)-vinyl | melting point 152-154° C. |
| 32 | fur-2-yl | melting point 154°-156° C. |
| 33 | phenyl | melting point 145° C. |
| 34 | 4-chlorophenyl | melting point 203°-204° C. |
| 35 | 3-trifluoromethylphenyl | melting point 145°-147° C. |
| 36 | 2-methylphenyl | melting point 101°-103° C. |
| 37 | 2-chlorophenyl | melting point 138°-139° C. |
| 38 | 2-methoxyphenyl | melting point 194° C. |
| 39 | cyclopropyl | melting point 46°-48° C. |
| 40 | thien-2-yl | melting point 153°-154° C. |
| 41 | dichloromethyl | melting point 86°-88° C. |
| 42 | ethoxycarbonyl | melting point 102°-103° C. |

TABLE 2

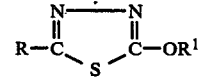

| No. | R | Physical Data |
|---|---|---|
| 1 | methyl | oil |
| 2 | H— | 32°/0.2 mbar |
| 3 | isopropyl | 62°/0.13 mbar |
| 4 | n-butyl | 85°/0.27 mbar |
| 5 | tert.-butyl | oil |
| 6 | vinyl | 39°/0.13 mbar |
| 7 | chloromethyl | |
| 8 | trichloromethyl | melting point 39° C. |
| 9 | 1-chloroethyl | 58°/0.27 mbar |
| 10 | 2-chloroethyl | 90°/0.27 mbar |
| 11 | trifluoromethyl | 55°/18.7 mbar |
| 12 | cyanomethyl | melting point 67° C. |
| 13 | methoxymethyl | oil |
| 14 | methoxyethyl | 84°/0.13 mbar |
| 15 | ethoxycarbonylmethyl | 107°/0.53 mbar |
| 16 | amino | |
| 17 | phenoxymethyl | melting point 44°-45° C. |
| 18 | 4-chlorophenoxymethyl | melting point 87° C. |
| 19 | 2,3-dimethylphenoxymethyl | melting point 108°-109° C. |
| 20 | 3,5-dichlorophenoxymethyl | melting point 141° C. |
| 21 | 2-methyl-4-chlorophenoxymethyl | melting point 107°-109° C. |
| 22 | 2,6-dimethylphenoxymethyl | oil |
| 23 | 4-tert.-butylphenoxymethyl | melting point 52°-54° C. |
| 24 | benzyl | melting point about 30° C. |
| 25 | 4-chlorobenzyl | melting point 36° C. |
| 26 | 3,4-dichlorobenzyl | melting point 65°-67° C. |
| 27 | 2,4-dichlorobenzyl | melting point 87° C. |
| 28 | 3-trifluoromethylbenzyl | oil |
| 29 | 3,4-dichloro-α-ethylbenzyl | oil |
| 30 | styryl | melting point 124°-126° C. |
| 31 | 2-(fur-2-yl)-vinyl | melting point 95°-98° C. |
| 32 | fur-2-yl | melting point 75°-77° C. |
| 33 | phenyl | |
| 34 | 4-chlorophenyl | melting point 108°-110° C. |
| 35 | 3-trifluoromethylphenyl | melting point 65°-67° C. |
| 36 | 2-methylphenyl | melting point 40°-42° C. |
| 37 | 2-chlorophenyl | melting point 60°-61° C. |
| 38 | 2-methoxyphenyl | melting point 68°-70° C. |
| 39 | cyclopropyl | oil |
| 40 | thien-2-yl | melting point 87°-89° C. |
| 41 | dichloromethyl | oil |
| 42 | ethoxycarbonyl | oil |

The majority of the compounds, prepared by the process according to the invention, of the formula I in Table 1, and the starting compounds of the formula II in Table 2 are novel.

What is claimed is:

1. In the process in which a 2-alkoxy-1,3,4-thiadiazole of the formula

in which R[1] is alkyl of 2 to 4 carbon atoms and R is (a) hydrogen; (b) unsubstituted alkyl; (c) alkyl substituted with one or more substituents selected from the group consisting of halo, cyano, alkoxy, alkylthio, alkylsulfinyl, alkylsulfonyl, alkylamino, alkoxycarbonyl, phenyl, phenoxy and phenylamino; (d) alkenyl; (e) phenylalkenyl; (f) cycloalkyl; (g) amino; (h) alkylamino; (i) dialkylamino; (j) alkoxycarbonyl; (k) alkylaminocarbonyl; (l) dialkylaminocarbonyl; (m) phenyl; or (n) a heterocyclic group selected from the group consisting of furyl, thienyl, pyrryl, isoxazolyl, oxazolyl, thiazolyl, isothiazolyl, pyridyl, pyrimidyl, benzofuryl, benzothienyl, indolyl, quinolyl and isoquinoline; is hydrolyzed to yield the corresponding 1,3,4-thiadiazol-2(3H)-one, the improvement which comprises treating said 2-alkoxy-1,3,4-thiadiazole with hydrogen chloride in non-aqueous organic solvent under nonaqueous conditions at a temperature of from 0° to 100° C.

2. The process according to claim 1 wherein the 2-alkoxy-1,3,4-thiadiazole is treated with hydrogen chloride at a temperature of from 20° C. to 60° C.

3. The process according to claim 1 wherein the solvent is diethyl ether, dioxane, chloroform, methylene chloride, methanol, ethanol or isopropanol.

* * * * *